United States Patent

Spears

(10) Patent No.: US 9,724,460 B2
(45) Date of Patent: Aug. 8, 2017

(54) CONTROLLED NUCLEATION FROM GAS-SUPERSATURATED LIQUID

(71) Applicant: Oakwood Healthcare, Inc., Dearborn, MI (US)

(72) Inventor: James Richard Spears, Bloomfield Hills, MI (US)

(73) Assignee: Oakwood Healthcare, Inc., Dearborn, MI (US)

( * ) Notice: Subject to any disclaimer, the term of this patent is extended or adjusted under 35 U.S.C. 154(b) by 362 days.

(21) Appl. No.: 14/224,788

(22) Filed: Mar. 25, 2014

(65) Prior Publication Data

US 2015/0273134 A1    Oct. 1, 2015

(51) Int. Cl.
| | |
|---|---|
| *A61M 5/00* | (2006.01) |
| *A61J 1/20* | (2006.01) |
| *B05B 7/04* | (2006.01) |
| *B65D 83/30* | (2006.01) |
| *A61M 13/00* | (2006.01) |
| *B65D 83/62* | (2006.01) |

(52) U.S. Cl.
CPC ............... *A61M 5/007* (2013.01); *A61J 1/20* (2013.01); *A61M 13/003* (2013.01); *B05B 7/0425* (2013.01); *B65D 83/303* (2013.01); *B65D 83/62* (2013.01)

(58) Field of Classification Search
CPC ........ A61J 1/20; A61M 5/007; A61M 13/003; B05B 7/0416; B05B 7/0425; B65D 83/303; B65D 83/62
USPC ...................................... 261/115, 116, 119.1
See application file for complete search history.

(56) References Cited

U.S. PATENT DOCUMENTS

| | | | |
|---|---|---|---|
| 4,659,384 A | 4/1987 | Daigo et al. | |
| 5,407,426 A | 4/1995 | Spears | |
| 5,797,874 A | 8/1998 | Spears | |
| 6,019,509 A | 2/2000 | Speckbrock et al. | |
| 6,180,059 B1 * | 1/2001 | Divino, Jr. ........... | A61M 1/1698 422/44 |
| 6,315,942 B1 * | 11/2001 | Spears ....................... | A23L 2/54 261/122.1 |
| 6,344,489 B1 * | 2/2002 | Spears ....................... | A23L 2/54 261/107 |
| 7,070,072 B2 * | 7/2006 | Bonham .............. | B65D 83/303 222/402.1 |

(Continued)

FOREIGN PATENT DOCUMENTS

| | | |
|---|---|---|
| EP | 2354037 A1 | 8/2011 |
| GB | 2443396 A | 5/2008 |

(Continued)

OTHER PUBLICATIONS

Agarwal, A.; Ng, WJ.; Liu, Y.; (2011) Principle and applications of microbubble and nanobubble technology for water treatment. Chemosphere. 84(9):1175-80.doi: 10.1016/j.chemosphere.2011.05.054. Retrieved on Oct. 16, 2013 from <http://www.ncbi.nlm.nih.gov/pubmed/21689840>.

(Continued)

*Primary Examiner* — Charles Bushey
(74) *Attorney, Agent, or Firm* — Harness, Dickey & Pierce, P.L.C.

(57) ABSTRACT

Disclosed is a system to generate bubbles. The bubbles may be formed to include a substantially or medically pure gas. The bubbles may be formed on demand and in a selected small size.

14 Claims, 3 Drawing Sheets

(56) References Cited

U.S. PATENT DOCUMENTS

| | | | |
|---|---|---|---|
| 7,199,085 | B2 | 4/2007 | Rea et al. |
| 7,214,508 | B2 | 5/2007 | Hucklenbroich et al. |
| 7,578,942 | B2 | 8/2009 | Yamasaki et al. |
| 7,632,400 | B2 | 12/2009 | Yamasaki et al. |
| 7,641,802 | B2 | 1/2010 | Yamasaki et al. |
| 7,691,268 | B2 | 4/2010 | Yamasaki et al. |
| 8,205,277 | B2 | 6/2012 | Yamasaki et al. |
| 8,317,165 | B2 | 11/2012 | Yamasaki et al. |
| 8,500,104 | B2 | 8/2013 | Spears et al. |
| 9,308,505 | B2* | 4/2016 | Spears ............ B01F 3/0446 |
| 2007/0095937 | A1 | 5/2007 | Noguchi et al. |
| 2007/0114176 | A1 | 5/2007 | Yamasaki et al. |
| 2007/0114183 | A1 | 5/2007 | Lee et al. |
| 2007/0119987 | A1 | 5/2007 | Vion |
| 2008/0277329 | A1* | 11/2008 | Zhang ............ C02F 1/24 210/220 |

FOREIGN PATENT DOCUMENTS

| | | |
|---|---|---|
| JP | 2012236151 A | 12/2012 |
| WO | WO-2004069153 A2 | 8/2004 |
| WO | WO-2007068446 A1 | 6/2007 |
| WO | WO-2013123524 A1 | 8/2013 |

OTHER PUBLICATIONS

Aggeli, C.; Giannopoulos, G.; Lampropoulos, K.; Pitsavos, C.; Stefanadis, C.; (2009) Adverse bioeffects of ultrasound contrast agents used in echocardiography: true safety issue or "much ado about nothing"? Curr Vasc Pharmacol. 7(3):338-46.Abstract.

Al-Kuhaili, M.F.; Durrani, S.M.A.; Khawaja, E.E; (2003). Optical properties of gallium oxide files deposited by electron-beam evaporation. AIP: Applied Physics Letters. Abstract.

All in one Micro-Nano Bubble Generators. Riverforest Corporation brochure. Retrieved on Oct. 16, 2013 from <http://www.riverforestcorp.com/micro-bubbles.html>. (6 pages).

Anderson, C.R.; Hu, X.; Tlaxca, J.; Decleves, A.; Houghtaling, R.; Sharma, MD, K.; Lawrence, M.; Ferrara, K.; Rychak, J.; (Apr. 2011), Ultrasound Molecular Imaging of Tumor Angiogenesis with an Integrin Targeted Microbubble Contrast Agent; Invest Radiol. 46(4): 215-224. doi:10.1097/RLI.0b013e3182034fed.; pp. 1-21.

Bommer, WJ; Shah, PM; Allen, H.; Meltzer, R; Kisslo, J.; (1984) The safety of contrast echocardiography: report of the Committee on Contrast Echocardiography for the American Society of Echocardiography. J. Am Coll Cardiol. 3(1):6-13.

Borden, M.A.; Qin, S.; Ferrara, K.W.; (2011). Ultrasound Contrast Agents. Molecular Imaging: Principles and Practice.Ch28, pp. 425-444.

Borisov, B.F.; Charnaya, E.V.; Gartvik, A.V.; Tien, C.; Kumzerov, Y.A.; Lavrentev, V.K., (2004). Peculiarites of gallium crystallization in confined geometry. Physics of the Solid State. vol. 46, No. 12. DOI: 10.1134/1.1841395. Retrieved on May 2012 from <http://www.springerlink.com> (7 pages).

Borisov, B.F.; Gartvik, A.V.; Kumzerov, Y.A.; Radzhabov, A.K.; Charnaya, E.V.; (Nov. 2001) Acoustic Studies of the Gallium Melting-Freezing Processes in Porous Matrices. X1 Session of the Russian Acoustical Society. pp. 145-148.

Borkent BM, Gekle S, Prosperetti A, and Lohse D. Nucleation threshold and deactivation mechanisms of nanoscopic cavitation nuclei. Physics of Fluids 21: 102003, 2009; pp. 1-9.The Advanced Barrier System™ (ABS) from CCL Container. Brochure. (4 pages), Aug. 2014.

Brereton GJ, Crilly RJ, Spears JR. Nucleation in small capillary tubes. Chemical Physics 230: 253-265, 1998.

Burns, W.A.; (Dec. 1999). Discovery of factors affecting bubble size in water. WaterTechnology.www.waternet.com. pp. 54-57.

Buttignoni, SC.; Khorsand, A.; Mundigler, G.; Bergler-Klein, J.; Heger, M.; Zehetgruber, M.; Baumgartner, H.; Binder, T. (Oct. 2004) "Agitated Saline versus polygelatine for the echocardiographic assessment of patent foramen ovale." J. Am. Soc. Echocardiogr. 17 (10): 1059-65. Abstract. <http://www.ncbi.n.m.nih.gov/pubmed/15452472>.

Cardozo, S.; Patel, H.; McGorisk, T.; Toosi, M.; Zalawadiya, S.; Alesh, I.; Kottam, A.; Afonso, L. Is Bacteriostatic Saline Superior to Normal Saline as an Echocardiographic Contrast Agent? Comparison of saline contrast agents. pp. 1-15, Aug. 2014.

Characterization of liquid-metal Galinstan® for droplet applications. (IEEE).Abstract, 2010.

Charnaya, E.V.; Tien, C.; Lee, M.K.; Kumzerov, Y.A.; (2010). Atomic mobility in nanostructured liquid Ga-In alloy. UIOscience. Abstract.

Charnaya, E.V.; Tien, C.; Lin, K.J.; Kumzerov, Y.A.; (Nov. 1998). X-ray studies of the melting and freezing phase transitions for gallium in a porous glass. The American Physical Society. Physical Review B., vol. 58 No. 17, pp. 11 089-11 092.

Cheng, D-C; Burkhardt, H.; Tracking Bubbles in High-Speed Image Sequences. Retrieved on Aug. 31, 2012 from Image Analysis of Bubbles in High-Speed Image Sequences; <http://lmb.informatik.uni-freiburg.de/people/cheng/Conf_PB2001_10_final.html>. (8 pages).

Chopra, A.; (2000) Microbubbles with a disteroylphosphatidylcholine, disteroylphosphatidylethanolamine-polyethyleneglycol (PEG) 2000-pyridyldithio propionate-PEG 40 stearate shell conjugated to cyclic arginine-glycine-aspartic acid-d-tyrosine-lysine (cRGD)pentapeptide. MICAD Molecular Imaging & Contrast Agent Database, pp. 1-5.

Contrast-enhanced ultrasound.definition.Wikipedia. Retrieved on Oct. 22, 2013 from <http://en.wikipedia.org/wiki/Contrast-enhanced_ultrasound>. (1 page).

Creech, J.; Divino, V.; Patterson, W.; Zalesky, PJ; Brennen, CE; (Dec. 2002). Injection of Highly Supersaturated Oxygen Solutions Without Nucleation. Journal of Biomechanical Engineering. DOI: 10.1115/1.1519558. pp. 676-683.

Definition. Focused ion beam. (Mar. 2012). <http://en.wikipedia.org>. Wikipedia. (8 pages).

Definition. Galinstan. (Feb. 2013).Wikipedia.http://en.wikipedia.org.(3 pages).

Dissolution Rate vs. Bubble (air) size. Atchley AA, Crum LA. In: Suslick KS.Ultrasound. VCH Pub,1988. (1 page).

Dixon SR, O'Neill WW, Bartorelli AL, Spears JR, David S, Grinberg I, Qureshi MA, Pepi M, Trabattoni D, Fabbiocchi F, Montorsi P, Marcovitz PA. Initial experience with Hyperoxemic Reperfusion after primary angioplasty for acute myocardinal infarction. JACC 39: 387-92, 2002.

Dynaflow—Bubble Generators brochure. Dynaflow, Inc. Retrieved on Oct. 16, 2013 from <http://www.environmental-expert.com/products/dynaflow-bubble-generators-146347>. (4 pages).

Fisher, NG.; Christiansen, JP.; Klibanov, A.; Taylor, RP.; Kaul, S.; Linder, JR; (2002), Influence of microbubble surface charge on capillary transit and myocardial contrast enhancement. J. Am Coll Cardiol. 40(4):811-9.

Garstecki, P.; Gitlin, I.; DiLuzio, W.; Whitesides, G.; Kumacheva, E.; Stone, H. (Sep. 2004). "Formation of monodisperse bubbles in a microfluidic flow-focusing device." Applied Physics Letter. vol. 85, No. 13, pp. 2649-2651.

Hydrosols and Microbubbles: Evaporation Suppression, Water Conservation, and Global Cooling (Jul. 2011). WaterWired. Retrieved on Oct. 23, 2013 from <http://aquadoc.typepad.com/WaterWired/2011/07/hydrosols-and-microbubbles.html>. (3 pages).

Jeon, D-S.;Luo, H.; Iwami, T.; Miyamoto, T.; Brasch, A.; Mirocha, J.; Naqvi, T.; Siegel, R. (2002) The Usefulness of a 10% Air-10% Blood-80% Saline Mixture for Contrast Echocardiography: Doppler Measurement of Pulmonary Artery Systolic Pressure. Journal of the American College of Cardiology. vol. 39. No. 1, 2002, ISSN 0735-1097/02/$22.00 PII S0735-1097(01)01698-9. pp. 124-129.

Jiang, C.; Li, X.; Yan, F.; Wang, Z.; Jin, Q.; Cai, F.; Qian, M.; Liu, X.; Zhang, L.; Zheng, H. (2012) Microfluidic-assisted formation of multifunctional monodisperse microbubbles for diagnostics and therapeutics. Abstract. Retrieved on Oct. 22, 2013 from IET Digital Library, <http://digitallibrary.theiet.org>. Micro & Nano Letters, vol. 6, I. 6, pp. 417-421, DOI: 10.1049/mnl.2011.0141.

(56) References Cited

OTHER PUBLICATIONS

Kaul, S.; (2008) Myocardial Contrast Echocardiography: A 25-Year Retrospective. American Heart Association, Inc. Circulation. 2008; 118:291-308.

Liu, T.; S., Prosenjit; Kim, C.-J. (Apr. 2012). "Characterization of Nontoxic Liquid-Metal Alloy Galinstan for Applications in Microdevices". Journal of Microelectromechanical Systems (IEEE). pp. 443-450. Doi:10.1109/JMEMS.2011.2174421.

Marriott, K.; Manins, V.; Forshaw, A.; Wright, J.; Pascoe, R.; (2012) Detection of right-to-left atrial communication using agitated saline contrast imaging: experience with 1162 patients and recommendations for echocardiography. J. Am Soc Echocardiogr. 26(a): 96-102. Doi: 10.1016/j.echo.2012.09.007.Epub Oct. 13, 2012 Retrieved from htpp://eprints.qut.edu.au/54461.

Marui, T.; An Introduction to Micro/Nano-Bubbles and their Applications. Nano Bubble Technologies LLC. General Manager, Technical Department (Futyu Laboratory). Tokyo, Japan. (6 pages), Aug. 2014.

Micro Bubble Nano Oxygen Water Generator. SC Wonderland. Retrieved on Oct. 16, 2013 from <http://www.sc88.com> (5 pages).

Micro-Nano Bubble generator built-in pump. Honda Pumps. Retrieved on Oct. 16, 2013 from <http://www.hondakiko.com.jp/english/microbubble/>. (2 pages).

Micro-nano bubble generators using nano porous polymer film. JETRO. Retrieved on Oct. 16, 2013 from <http://www.jetro.go.jp/ttpp/EAN.CR07>. (2 pages).

Nahra, H.; Kamotani, Y.; (2003) Prediction of bubble diameter at detachment from a wall orificein liquid cross-flow under reduced and normal gravity conditions. Chemical Engineering Science 58 (2003) 55-69.

Naidich, Y.V.; Zhuravlev, V.S.; Chuvashov, Y.N.; (1975). Nature of the Adhesion of Gallium Solders to Oxide Materials. Test Methods and Properties of Materials. Power Metallurgy and Metal Ceramics (1974). vol. 13, No. 12; DOI: 10 1007/BF00807911.Retrieved Apr. 2012 from <http://resources.metapress.com>. (1 page).

Nano Bubble Generator. Nano Bubble Generator—Negatron Co., Ltd. Retrieved on Oct. 16, 2013 from <http://negatron.en.ec21.com/Nano_Bubble_Generator>. (3 pages).

O'Neill WW, Martin JL, Dixon SR, Bartorelli AL, Trabattoni D, Oemrawsingh PV, Atsma DE, Chang M, Marquardt W, Oh JK, Krucoff MW, Gibbons RJ, Spears JR; AMIHOT Investigators. Acute Myocardial Infarction with Hyperoxemic Therapy (AMIHOT): a prospective, randomized trial of intracoronary hyperoxemic reperfusion after percutaneous coronary intervention. J Am Coll Cardiol 50: 397-405, 2007. Epub Jul. 16, 2007.

Rodrigues, RT; Rubio, J.; (2003). New basis for measuring the size distribution of bubbles. Minerals Engineering 16. pp. 757-765.

Sato, K.; (Sep. 2011) Recent Patents on Micro- and Nano-Bubble Applications and Potential Application of a Swirl-type Generator. Recent Patents on Mechanical Engineering. vol. 4 I. 3, p. 202. Retrieved from <http://connection.ebscohost.com/c/articles/66703764 on Oct. 16, 2013. (1 page). Abstract.

Seitz, R.; Bright Water. Hydrosols, Water Conservation and Climate Change. (Aug. 2010). Department of Physics Harvard University. (20 pages).

Soliman, O.; Geleijnse, M.; Meijboom, F.; Nemes, A.; Kamp, O.; Nihoyannopoulos, P.; Masani, N.; Feinstein, S.; Ten Cate, F.; (2007). The use of contrast echocardiography for the detection of cardiac shunts. Eur J Echocardiography, 8, S2-S12.

Spears JR, Henney C, Prcevski P, Xu R, Li L, Brereton GJ, DiCarli M, Spanta A, Crilly RJ, Sulaiman AM, Hadded S, Lavine S, Patterson WR, Creach J, Vander Heide R. Aqueous Oxygen Hyperbaric Reperfusion in a Porcine Model of Myocardial Infarction. J. Invasive Cardiology 14: 160-166, 2002.

Spears JR, Prcevski P, Brereton GJ. Aqueous oxygen near the homogeneous nucleation limit of water: stabilization with submicron capillaries. ASAIO Journal 52: 186-191, 2006.

Spears JR, Prcevski P, Jiang A, Brereton GJ, and Vander Heide R. Intracoronary aqueous oxygen perfusion, performed 24 hrs after the onset of postinfarction reperfusion, experimentally reduces infarct size and improves left ventricular function. International J Cardiol 113-371-5, 2006.

Spears JR, Prcevski P, Xu R, Li L, Brereton G, DiCarli M, Spanta A, Crilly R, Lavine S, and vander Heide R. Aqueous Oxygen Attenuation of Reperfusion Microvascular Ischemia in a Canine Model of Myocardial Infarction. ASAIO Journal 49: 716-720, 2003.

Spears JR, Wang B, Xu X, Prevski P, Jiang AJ, Spanta A, Crilly R, Brereton GJ. Aqueous Oxygen: a highly O2-supersaturated infusate for regional correction of hypoxemia and production of hyperoxemia. Circulation 96:4385-4391, 1997.

Spears JR. Advances in the Management of Respiratory Failure. Aqueous preparations of oxygen. ASAIO J. 42:196-198, 1996.

Stone GW, Martin JL, de Boer M-J, Margheri M, Bramucci E, Blankenship JC, Metzger DC, Gibbons RJ, Lindsay BS, Weiner BH, Lansky AJ, Krucoff MW, Fahy M, Boscardin WJ and for the AMIHOT-II Trial Investigators. Effect of supersaturated oxygen delivery on infarct size after percutaneous coronary intervention in acute myocardial infarction. Circulation: Cardiovasc Intervent 2: 366-375, 2009.

Stride, E.; Saffari, N.; (2003) Microbubble ultrasound contrast agents: a review. Proc. Instn Mech. Engrs vol. 217 Part H: J. Engineering in Medicine. pp. 429-447.

Swanson, E.; Mohan, V.; Kheir, J.; Borden, M.; (2010) Phospholipid-Stabilized Microbubble Foam for Injectable Oxygen Delivery. Langmuir. Abstract. Retrieved on Jan. 7, 2013 from <http://pubs.acs.org/doi/abs/10.1021/Ia1029432>.

Talu, E.; Lozano, M.; Powell, R.; Dayton, P.; Longo, M.; (Nov. 2006) Long-Term Stability By Lipid Coating Monodisperse Microbubbles Formed by a Flow-Focusing Device. Langmuir, 22(23): 9487-9490. pp. 1-10.

Tretheway, D.; Liu, X.; Meinhart, C.; (2002) Analysis of Slip Flow in Microchannels. Phys. Fluids 14:L9-L'. (8 pages).

Wang, S.; Dhanaliwala, A.; Chen, J.; Hossack, J.; (2013) Production rate and diameter analysis of spherical monodisperse microbubbles from two-dimensional, expanding-nozzle flow-focusing microfluidic devices; American Institute of Physics DOI:http://dx.doi.org/10.1063/1.4774069. pp. 1-5.

Zimmerman, W.B.; Tesar, V.; Butler, S. ; Bandulasena, HC.; Microbubble Generation. Department of Chemical and Process Engineering, University of Sheffield, Mappin Street, Sheffield S1 3JD, United Kingdom. (13 pages), Aug. 2014.

International Search Report and Written Opinion mailed on Jul. 3, 2015 for PCT/US2015/022237 claiming benefit of U.S. Appl. No. 14/224,788, filed Mar. 25, 2014.

International Preliminary Report on Patentability and Written Opinion mailed Oct. 6, 2016 for PCT/US2015/022237 which claims benefit of U.S. Appl. No. 14/224,788, filed Mar. 25, 2014.

\* cited by examiner

FIG. 6

CONTROLLED NUCLEATION FROM GAS-SUPERSATURATED LIQUID

FIELD

The subject disclosure relates to directing a flow of a liquid through a tube, and particularly to formation of bubbles in a flow of the liquid.

BACKGROUND

This section provides background information related to the present disclosure which is not necessarily prior art.

In various applications, it is desirable to deliver a gas to a subject for a selected purpose. A gas may be provided to saturate a liquid, fill a volume, etc. The gas may be delivered via a bubbler or similar apparatus.

Providing a volume or number of bubbles to a volume, such as a human subject, can be used for various procedures. In some examples, providing a volume of bubbles to a subject can be used as an echogenic contrast agent. Bubbles may be created by the agitation of a solution, such as saline, by reciprocating connected syringes and injecting the results into bubble volume. For example, agitated air in saline and agitated air in blood and saline mixtures can generate bubbles that are introduced intravenously. Agitation methods can generate bubbles in the range of 26 µm to 32 µm, as disclosed in Doo-Soo Jeon, M. D. et al., "The usefulness of a 10% air-10% blood-80% saline mixture for contrast in echocardiography, Doppler Measurement of Pulmonary Artery Cystolic Pressure", J Am Coll Cardiol, 39:1, p. 124-129 (January 2002).

SUMMARY

This section provides a general summary of the disclosure, and is not a comprehensive disclosure of its full scope or all of its features.

In preparing for and/or performing a procedure on a subject, such as a human patient subject, various imaging techniques can be used. Certain imaging techniques may require or be enhanced by the use of a contrast agent. For example, a plurality of bubbles, of a selected size, can be positioned in a volume to enhance echogenic contrast within the volume. The generation of bubbles can be formed in various manners, such as generation of gas bubbles from nucleation sites in a flow of a liquid.

The liquid, which may be referred to as a carrier liquid, can be saturated with a selected gas and placed in a container. The selected gas can include oxygen, such as gaseous and molecular oxygen. The oxygen gas may be substantially pure and/or sterile. Pure oxygen may be oxygen gas that is generally provided for use in a medical procedure and appropriate for injection into a vascular system of a human subject. The liquid can include any appropriate liquid, such as sterile saline, lactated ringer, 5% dextrose saline, or other sterile materials.

The liquid having the gas dissolved therein can be held in a container. The container may be sealed to prevent escape of gas and liquid such that the saturated liquid can be held at pressure in a container for an extended period of time. The container can include multiple walls to assist in sealing and containing the liquid and gas within the container.

A delivery tube can be interconnected with the container to allow delivery of the carrier liquid that is saturated with the gas at a selected rate. The tube can include a selected internal diameter, generally in the range of a capillary tube. The tube may be coated with a selected material, as disclosed herein, to provide for a plurality of nucleation sites for formation of small bubbles. The small bubbles can be injected or provided to a delivery area, such as to a patient, for delivering a plurality of bubbles to the patient to be used as a contrast agent. The bubbles may remain viable as a contrast agent without having an external surface coating (e.g., a lipid or phospholipid coat) for a selected period of time. It is understood, however, that a selected material (e.g. a surfactant) may be added). The bubble size can be selected based upon the size of the tube and/or the concentration of the gas in the liquid and other characteristics, such as a flow rate.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
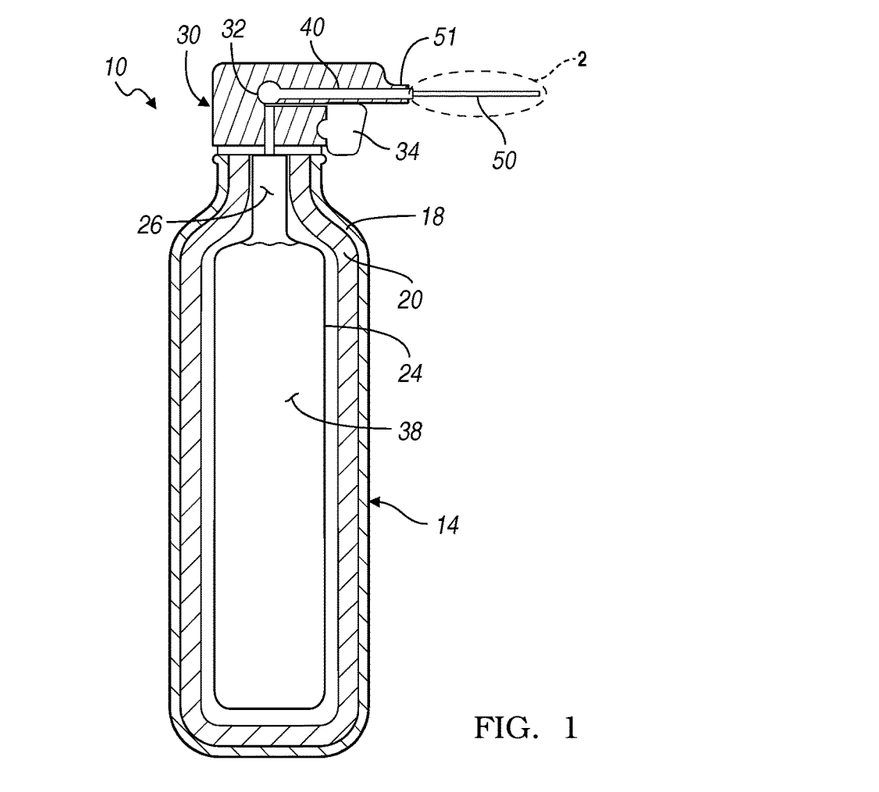
FIG. 1 is a cross-section view of a container, according to various embodiments.

A plurality of bubbles can be generated with a system, such as a bubble delivery system 10 illustrated in FIG. 1. It is understood that a plurality of bubbles can fill a volume by being placed in the volume for various purposes, such as those described further herein. Various medical procedures can be enhanced or augmented with bubbles generated by the bubble generation system 10, such as ultrasound imaging. It is understood, however, that non-medical procedures can also be augmented or enhanced with bubbles generated from the bubble generation system 10. For example, imaging of non-living subjects, including mechanical voids, conduit structures, such as hydraulic conduits, and other non-anatomical structures can be imaged. Further, the bubble generation system 10 can be provided to generate bubbles at any appropriate time and for any appropriate procedure, such as delivering a gas for a non-medical procedure (e.g. oxygenating a volume of water). Accordingly, although a medical procedure is described exemplary herein, it is understood that non-medical procedures, including those that do not involve a human patient or subject, can also be performed using the bubble generation system 10.

For some applications, such as cleaning of surfaces, the bubble generation system 10 can be used for non-surgical and/or surgical medical applications including cleaning of skin, wounds, and dental surfaces, and for non-medical applications.

Generally, the bubble generation system 10 can include a container 14. The container 14 can include a single or double wall container of appropriate construction. As exemplary illustrated in FIG. 1, the container 14 can include an outer wall or first wall 18 and a second wall or inner wall 20. Both the walls 18, 20 can be formed of a single material such as stainless steel, aluminum, or other appropriate metal or metal alloys. It is understood that the container 14 can be formed in an extrusion or mold, but any appropriate formation can be used. The container 14 can further include an internal flexible liner 24. The flexible liner 24 can be formed of an appropriate material that can generally seal both liquid and gas. In various embodiments, the flexible liner 24 can be placed within the container 14. A material, such as a gas saturated liquid, may be placed within the flexible liner 24. Thus, the liner 24 contains the saturated liquid within the container 14. The material contained within the flexible liner 24 can be an appropriate material such as a gas saturated liquid, including sterile saline.

It would be understood, by one skilled in the art, that the container 14 need not include the internal flexible container 24. The container 14 including the walls 18, 20, can generally be formed in a substantially liquid and gas tight form. Generally, a metal walled container, for example a double wall container, can generally be impervious to liquid and gaseous escape. Appropriate containers can include the Advanced Barrier System™ (ABS) containers sold by CCL Container, having a place of business in Hermatige, Pa., USA.

In communication with an internal volume of the container 14, including an internal volume 26 of the flexible liner 24, can be a trigger or nozzle mechanism 30. The trigger mechanism 30 can include a valve 32 that can be operated with a button or trigger 34 to allow flow of a material 38 from the flexible liner 24 through a passage 40 and a directing or bubble generation tube 50. The bubble generation tube 50 is described in further detail herein. Initially, the bubble generation tube 50 may allow for generation of a plurality of bubbles during and after passage of the material 38 from the flexible liner 24 passes through the bubble generation tube 50.

The system 10, discussed above, including the volume of gas saturated liquid can be provided with the nozzle 30 to produce a plurality of bubbles for a selected purpose. The gas saturated liquid can include appropriate liquids, such as sterile saline, lactated ringer, reverse osmosis filtered water, or other appropriate liquids. The liquid may be placed within the container 14 at a selected pressure. The container fill pressure may be about 50 pounds per square inch (psi) to about 500 psi, including about 100 psi to about 400 psi, and further including about 300 psi. Depressing the trigger 34 may open the valve 32 to allow the pressurized liquid to exit through the tube 50 due to a difference in pressure between the fill pressure and the external atmospheric pressure.

Further, the liquid may be saturated to a selected degree or amount with a selected gas. As discussed herein, exemplary gasses may include medical purity molecular oxygen. The amount or saturation of the gas in the liquid may be defined by the partial pressure of the gas within the liquid. The partial pressure of the molecular oxygen may be provided at about 5 bar (about 72 psi) to about 30 bar (about 435 psi), and further about 5 bar to about 20 bar (about 290 psi), and further about 8 bar (about 116 psi) to about 10 bar (about 145 psi) partial pressure of the molecular oxygen. Oxygen ($O_2$) at about 50 bars (about 725 psi) corresponds to about 1.5 milliliters of oxygen per gram of water. Various systems for saturating the liquid can include those disclosed in U.S. Pat. No. 8,500,104 to Spears et al., incorporated herein by reference.

The tube 50 can be connected to the nozzle 30 in any appropriate manner, including those generally known in the art. For example, the tube 50 may be friction fit at a first or proximal end 50a within a nozzle nose 51. A locking or catch system, such as interlocking threads between the tube 50 and the nose 51 may also be provided.

Figure 2:
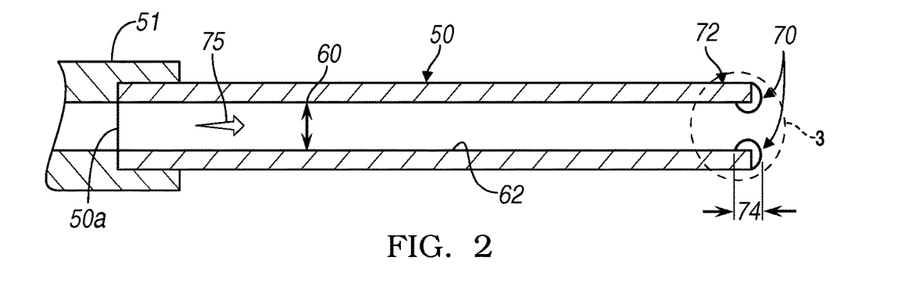
FIG. 2 is a cross-section view of a delivery tube, according to various embodiments.

The tube 50 can be formed to include appropriate properties to allow for formation of a selected amount of bubbles in a selected size based upon properties of the tube 50. For example, the tube 50 can be formed to have an internal diameter 60 that is about 40 μm (micrometers) to about 150 μm, including about 80 μm to about 110 μm, and further including about 100 μm. The internal diameter 60 of the tube 50 allows for a selected flow rate. The selected flow rate may including a velocity that does not exceed a Reynolds number that results in turbulent flow. Generally, it is understood that a Reynolds number that is between about 2200-2400 indicates the onset of turbulent flow. However, with an internal diameter of 100 μm or less, flow rates of 5-20 meters per second (m/sec.) can be achieved through the tube 50 without reaching turbulent flow. The Reynolds number is also based upon various factors including the velocity of the fluid, the density and velocity of the fluid flowing through the tube, and the dimensions of the tube.

The tube 50 can also be formed of selected materials such as silica or fused silica to form an internal wall 62 that has a substantially smooth and crevice free surface 63. The surface 63 may be understood to be substantially smooth or crevice free when the surface 63 does not include nucleation sites for bubbles having an average size greater than about 30 μm when a liquid passing through the tube 50 at a rate of about 5-20 m/sec. that has a dissolved oxygen partial pressure of about 8 bars to about 140 bars (about 2030 psi). Accordingly, the smooth surface 63 and/or the wall 62 may include crevices that are substantially small or inconsequential for nucleation of bubbles within the tube 50 during passage of the fluid having the dissolved gas therein. The surface 63 of the wall 62, therefore, may generally have a crevice of less than 1 μm in width and/or depth extending into the wall 62.

The tube 50, as illustrated in FIG. 2, may have a nucleation coating 70. The nucleation coating may include a hydrophilic and/or a hydrophobic material, as discussed further herein. In various embodiments, a hydrophilic material may form or create hydrophobic regions or domains. As discussed herein, a hydrophobic domain may include a small crevice or edge that allows for bubble nucleation.

As various examples, the coating 70 may be formed of a material including amorphous metals, such as gallium or an appropriate alloy of gallium (such as gallium-indium-tin). The coating 70 can be understood to be formed at substantially only the exit or distal end 72 of the tube 50 such as by dipping or placing the amorphous metal at the end 72 of the tube 50. Accordingly, the coating 70 may extend a distance 74 into the tube 50, but need not extend a long distance into the tube 50 or cover a great extent thereof. In various embodiments, the coating only extends a selected distance into the tube 50 along the surface 63, as discussed herein. Further, the coating 70 may be understood to include a plurality of individual or separated islands or dots 70a. Thus, a continuous layer of the coating 70 may not be present and need not be present for purposes of the bubble generation system 10.

For example, length 74 of the coating 70 may extend about 0.1 millimeters (mm) to about 5 mm, including about 0.5 mm to about 4 mm, and further including about 1.5 mm to about 2.5 mm, and further including about 2 mm. For example, the coating 70 may cover an exterior end wall and the selected length of the surface 63 within the tube 50. The surface 63 may define a throughbore or internal bore within the tube 50. The coating 70, however, may have the length 74 of less than about 2 mm into the tube 50. The length 74 of the coating 70, however, may alternatively be about 1 mm, including about less than 0.5 mm, and further including less than about 0.1 mm into the tube 50.

Thus, the coating 70 may coat substantially the tube end 72 and the distance 74 into the tube 50, such as about 0.1 mm to about 5 mm. In various embodiments, the coating 70 only extends the selected distance, such as about 0.1 mm to about 5 mm, including only about 2 mm into the tube 50. Accordingly, as the saturated liquid flows, generally in the direction of Arrow 75, it will contact the coating 70. The coating 70 may cause nucleation and/or formation of bubbles thereon. Without being bound by the theory, it is believed that the liquid, such as water, will wet all crevices or openings of the coating 70 that are generally larger than a few nanometers to a few hundred nanometers. The nanometer sized crevices may contain gas pockets that allow growth of submicron bubbles as the gas-supersaturated liquid passes over the coating 70. The crevices may also be hydrophobic domains for bubble nucleation. As discussed further herein, the formation of bubbles at these nanometer crevices allow for formation of small bubbles for various purposes.

As noted above, the velocity of the liquid through the tube 50 can be at a substantially high rate, such as about 5 m/sec. to about 20 m/sec. To form bubbles of a selected size, such as in a range of a few micrometers to less than 1 μm, including about 0.1 μm to about 10 μm, and further including less than about 7 μm, the saturation of gas in the liquid can be selected to be substantially high. For example, a partial pressure saturation of a sparingly soluble gas (such as oxygen, air, nitrogen) in the liquid can be about 6 bars to about 150 bars, including about 8 bars to about 100 bars, and further including about 8 bars to about 20 bars. The saturation of gas in the liquid at a high partial pressure can allow for the formation of bubbles at substantially small nucleation sites within the tube 50.

Figure 3:
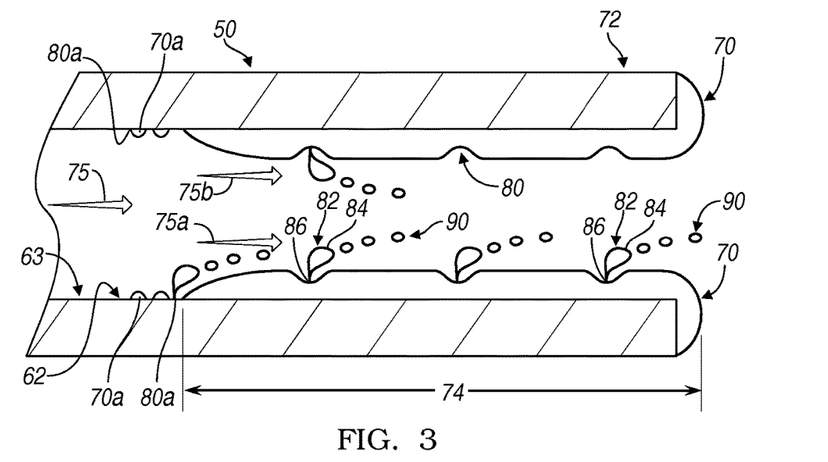
FIG. 3 is a detail cross-section of the delivery tube of FIG. 2.

As illustrated in FIG. 3, the coating 70 placed on the tube 50 can include and/or define nucleation sites 80. The nucleation sites 80 may allow the nucleation of bubbles or initiated bubbles 82. As noted above, the nucleation sites may be hydrophobic regions or domains that allow for bubble nucleation. Thus, even when the coating 70 is hydrophilic, the nucleation sites 80 may be locally hydrophobic. In other words, the nucleation sites 80 are not wetted by the water or liquid carrying the gas that forms the bubbles.

The initiated bubbles 82 may have a head portion 84 and a neck portion 86. The neck portion 86 can generally be formed within the nucleation site 80, which may include a crevice or a defect of the coating 70. It is understood, however, that bubble formation may also be formed at any nucleation site, such as an interface of the coating 70 with the surface 63 of the tube 50. The interface may include or be referred to as an edge nucleation site 80a, which also may be hydrophobic domains. The dots 70a may form a plurality of the edge nucleation sites 80a in the tube 50. According to various embodiments, the dots 70a may be the only coating portion of the material 70 within the tube 50 and all of the nucleation sites may be on the dots 70a.

As the bubbles grow, such as due to the high pressure of gas in the liquid, they can be sheared or broken from the nucleation site 80 to form a small bubble 90. The small bubbles 90 may have the size as noted above, including less than about 7 μm as measured with optical inspection. The bubbles 90 can be formed as a trail of bubbles from the nucleation site 80. The trail of bubbles will generally flow in the direction of the flow of the liquid as indicated by the direction of Arrow 75.

As noted above, the flow of the liquid through the tube 50 can generally be a laminar that is completely turbulent flow free or substantially turbulent free flow. Thus, a boundary layer flow near the surface 63 of the tube can assist in shearing the bubbles 90 when they are generally small and not have formed into larger bubbles. As noted above, the laminar flow formed within the tube 50 can be defined by the diameter 60 of the tube, flow rate, and other generally known factors relating to a Reynolds number within the tube 50.

Further, the laminar flow can assist in reducing coalescence or agglomeration of individual bubbles into larger bubbles by reducing the possibility of contact between bubbles. Further, the small size of the formed bubbles also reduces the possibility of coalescence into a larger bubble. Generally, the small bubbles have a high surface tension and resist coalescing. Thus, as each bubble is formed and sheared off near the neck 86, the individual bubbles 90 can move in the direction of the flow arrow 75 out the free or open end 72 of the tube 50.

Further, as noted above, the internal diameter 60 being selected in a range of about 100 μm can substantially ensure a high velocity at the interface of the surface 63 and the liquid flowing through the tube 50. A larger internal diameter may allow for a slow movement of the liquid near the interface with the internal surface 63 of the tube 50, which may allow for a greater time for the bubblehead 84 to grow prior to being sheared by the flow of the liquid. Further, the high flow rate of the liquid can allow for a very rapid formation and detachment of bubbles due to the growth of the bubbles at the high partial pressure of the gas. Thus, a larger amount of bubbles can be formed very quickly through the high flow rate, the high velocity at the interface of the liquid and the walls or the surface of the coating 70, as indicated by the Arrow 75a and 75b, the high pressure of the gas dissolved in the liquid, and the submicron nucleation sites 80 formed at the coating 70.

As noted above, the coating 70 can be formed of a substantially hydrophobic or hydrophilic material. According to various theories, a hydrophilic material that is substantially or completely smooth may allow for the growth of a large bubble due to the hydrophilic nature of the coating by maintaining contact of the liquid with the coating. A hydrophilic coating having focal nanoscopic hydrophobic regions or domains, however, may allow for the formation of a small bubble at a hydrophobic region or domain that can detach quickly as there is a low affinity for the liquid at the hydrophobic region, such as the nucleation site 80 that may include a small crevice, such as a sub-micron or nanometer size crevice or defect. Further, the non-wetting or non-affinity to wetting of the small or submicron crevices 80 may allow for the formation of a bubble therein as the crevices are not wetted by the liquid in the flow and a nucleation site for the gas within the liquid can be provided. Larger crevices in the coating 70 may be better wetted and/or filled with the liquid and not allow for an efficient nucleation site for a bubble. It is understood, also, that small crevices, such as crevices that are sub-micron is size, may be formed in any appropriate manner to form the bubbles 90.

Some static systems such as those discussed in Borkent B M, Gekle S, Prosperetti A, Lohse D, "Nucleation threshold and deactivation mechanisms of nanoscopic nuclei", arXiv: 0906.055v1 [physics.flu-dyn], 2 Jun. 2009 form bubbles using acoustic waves in a static volumes. Borkent discusses and observes deactivation of nanoscopic nucleus sites by wetting of crevices from collapse of a bubble into the crevice during acoustic cavitation. At least in contrast to Borkent, the system 10 rapidly removes bubbles 90 from nucleation sites 80 by high velocity flow of the gas supersaturated liquid and an absence of bubble collapse do not allow the mechanism observed by Borkent to deactivate nucleation sites.

Further, the bubbles formed at the nucleation sites 80, which may be micrometer fractures or crevices, may be further inhibited to grow within the flow of the liquid through the tube 50. For example, reduced engagement or collision with other bubbles in the laminar flow and the reduced parabolic flow front through the substantially narrow internal diameter of the tube 50. Further, the small bubbles being formed at the nucleation sites 80 have an internal gas pressure that is substantially high to further reduce possible coalescence or agglomeration of multiple bubbles during or following a collision.

Further, the formation or positioning of the coating 70 substantially at the distal end of the tube 50 allows for only a minimal time of the bubbles 90 be present within the tube 50. In particular, as noted above the coating may extend at most about 5 mm, and further at most 2 mm into the tube 50. If the rate of flow of the liquid is even only 5 m/sec, the bubble 90 formed at the most proximal portion of the coating 70 is present within the tube 50 for about 0.0004 sec. to about 0.001 sec.

Figure 4:
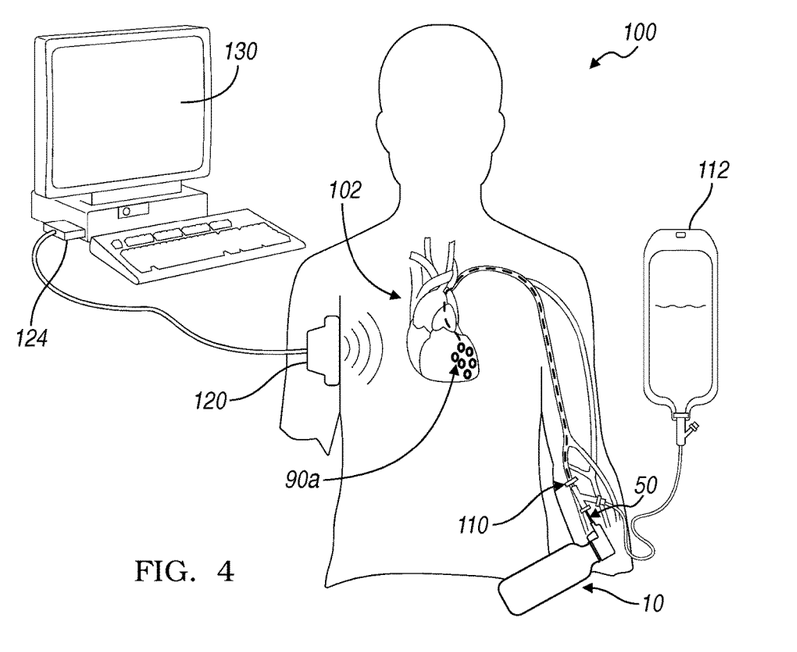
FIG. 4 is a schematic environmental view of delivery of a plurality of bubbles.

As discussed further herein, as illustrated in FIG. 4, the bubbles 90 can be introduced into a subject, such as a human patient 100. Accordingly, the bubbles will exit the volume of the tube 50 substantially rapidly, due to the high flow rate of the liquid through the tube 50, generally in the direction of Arrow 75, and enter into a second volume such as the patient 100 or another delivery vessel. As discussed above, the coating 70 can be positioned at the distal end 72 of the tube 50, such as generally the distance 74 into the internal diameter of the tube along the surface 63. Accordingly, the distance 74 can be short and the coating 70 placed substantially near an end of the tube 50 to allow for the creation of the bubbles 90 substantially at the end of the tube 50. Thus, the formed bubbles 90 are caused and allowed to substantially quickly exit the bore of the tube 50.

According to various embodiments, as discussed above, the bubbles 90 can be placed within a volume, such as within a volume of a patient 100. The bubbles 90 may form a volume or plurality of bubbles 90a within a selected volume of the patient 100, such as within a volume of a selected chamber of a heart 102 of the patient 100. The bubbles can be introduced through a vascular puncture 110, such as one provided with an IV 112. The bubbles can be introduced from the container 10 through the tube 50 in to the puncture and travel to the volume of the heart 102.

Figure 4A:
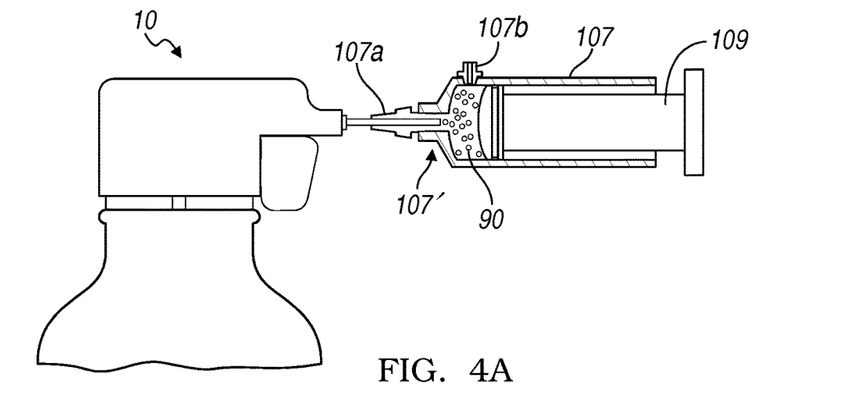
FIG. 4A is a schematic view of initially forming bubbles in a syringe.

The bubbles 90 may also be first introduced into a delivery device, such as a syringe barrel 107 that may include a plunger 109, as generally known in the art. The generated bubbles may be introduced through a distal port 107a and/or a side portion 107b. Both the distal portion 107a and the side port 107b may be near a distal end 107' of the syringe 107. This may allow the bubbles 90 to be formed and/or congregate in the distal region of the volume of liquid in the syringe. Thus, as the liquid from the syringe 107 is delivered to the subject, such as the patient 100, the volume of liquid with the bubbles is followed or chased by a volume of liquid that is bubble free. This may help ensure that the entire volume of bubble containing liquid reaches the selected location, such as the heart 102.

The generated bubbles in the syringe 107 may then be introduced into a selected volume, such as the patient 100. As an example of delivery, once the bubbles are formed and placed in the syringe 107, they can be injected into a patient as a single bolus or over a period of time, such as a few seconds, such as with delivery of the syringe 107. It is further understood, however, that the patient 100 need not be the only receiver of the bubbles 90. Nevertheless, in a human or oxygen metabolizing subject if capillaries in any organ are blocked by oxygen microbubbles, the deoxyhemoglobin binds the oxygen and the tissues metabolize the gas to reverse local ischemia. Thus, the procedure and bubbles 90 produced with substantially or medically pure oxygen product are useful in multiple ways. For example, the bubbles may be generated efficiently by injecting the oxygen enriched or saturated liquid into the syringe 107 or patient 100, thus allowing a quick bubble generation. This is also simpler, easier, and more rapid than agitating an air and saline mixtures. Further, the device 10 can be used to generate the bubbles 90 in a sterile manner and avoid a potential infection.

An image system, such as an ultrasound transducer 120 can be used to acquire images of the heart 102. The bubbles 90a positioned with the volume of the heart 102 can act as a contrast agent for the ultrasound transducer system 120. The ultrasound transducer 120 can be interconnected with an ultrasound imaging system 124, such as the SONOS™ Ultrasound Imaging System sold by Hewlett-Packard, An image can then be displayed on a display device, such as a computer screen 130. The image can be enhanced with the bubbles 90a acting as a contrast agent within the volume of the heart 102 to allow for a clear view of a volume of a heart 102. It is understood that other selected organs of the patient 100 can also be imaged with the ultrasound transducer 120 with the use of the bubbles 90a as a contrast agent. The bubbles 90a, as noted above, may be the bubbles 90 formed with the bubble generation system 10 that have been introduced into a selected volume.

In various embodiments, the bubbles may be generated with the system 10 and delivered directly to the patient 100 or subject. Thus, the bubbles may be generated substantially contemporaneously with the introduction or use of the bubbles. Thus, the bubbles need not be formed in a solution and stabilized, such as with other compounds. The bubbles can be formed on demand with the system 10. The bubbles, once introduced, may be used as a contrast agent within the volume being imaged.

It is further understood that an introduction of the bubbles 90 into a human patient 100 is not required. For example, ultrasound imaging can be performed on any appropriate system, such as any mechanism that allows for ultrasound imaging for inspection within a volume. Various examples can include ultrasound inspection of containers, mechanical devices, or other appropriate systems. Accordingly, it is understood by one skilled in the art that introduction of the bubbles 90 into a human subject is not required and that the bubbles can be introduced into any appropriate subject, such as a non-human or non-living subject, for contrast enhancement.

Figure 5:
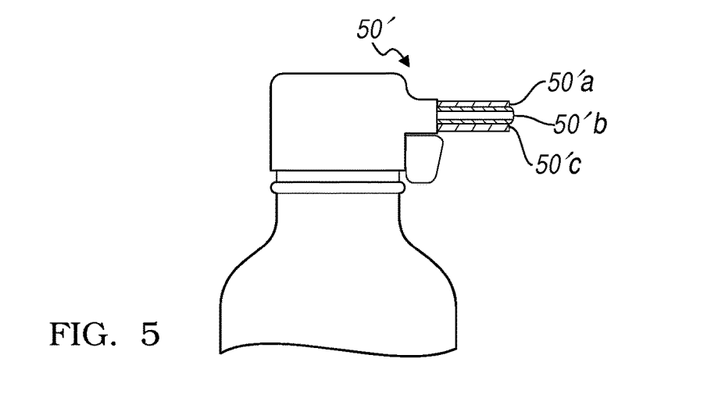
FIG. 5 is a schematic illustration of a delivery system with multiple tubes.

According to various embodiments, the container 10 can include more than one of the tubes 50 interconnected with the nozzle 32. For example, a plurality of the tubes 50, as illustrated in FIG. 5, can be positioned substantially parallel to one another to allow for a high volume ejection of a liquid and bubbles from the container 10. The plurality of tubes 50' (for example including a first, second, and third tube 50'a, 50'b, and 50'c) can be provided in parallel and include the features, as discussed above, including each including the coating 70.

Figure 6:
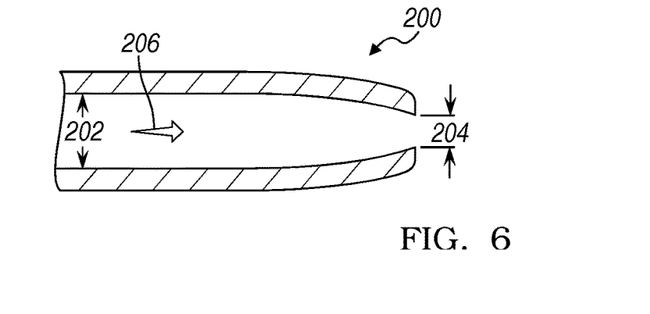
FIG. 6 is a cross-section view of a tube according to various embodiments.

According to various embodiments, as exemplarily illustrated in FIG. 6, when an echo contrast agent is used to visualize the heart 102 (including evaluation of the presence of a right to left shunt from, for example, a PFO [patent foramen ovale]), a mean bubble size generally in the range of about 40 micrometers to about 60 micrometers may be used. In this case, a tube 200, such as a type of capillary material and the geometry of a lumen through the tube 200 at or near a distal end of the capillary can be selected to generate suitable microbubbles of oxygen from supersaturated physiologic aqueous liquids, without the need for a capillary lumen surface coating. For example, a nitinol tubing 200 about 6 inches (about 15 centimeters) long with an internal diameter 202 of about 100 micrometers (microns) (about 0.004 inches) and an outer diameter of about 0.011 inches (about 0.28 millimeters) can be used to generate bubbles about 40 micrometers to about 60 micrometers, in the following manner. The nitinol tubing may be formed of a selected titanium alloy. Saline or water supersaturated at 250 psi with oxygen, driven hydrostatically at 350 psi through the nitonol tubing generally in the direction of arrow 206 with about the distal terminal end of the tubing of about 1 mm or less being crimped generated the bubbles of about 40 micrometers to about 60 micrometers. The tubing may be crimped by cutting the tubing with sharp titanium scissors.

During investigation, a mean bubble size of approximately 10 microns to approximately 15 microns is produced as a dense echogenic cloud of microbubbles when infused into a 500 mL beaker of water through the crimped nitonol tubing described above. Investigation occurred by viewing at high magnification with a 40 nanosecond strobe light (such as that sold by Sugawara Labs, Japan). The luminal area at the distal end of the nitinol tubing is crimped to have a crimped internal diameter 204 to about 40% of the original luminal area, and deformed into an elliptical/slit-like shape. In the elliptical shape, the internal diameter 204 may be a minor axis of an ellipse formed by the tube 200 in cross-section at the distal end. The crimping reduces the liquid flow rate to about 5 mL/min from a value of about 6 mL/min before the crimping. The velocity is therefore markedly increased by the crimping, resulting in an increase in effluent velocity which produces a Reynold's number exceeding the onset of turbulent flow (approximately greater than about 2200). Without crimping the tubing, microbubble formation is negligible because the lower flow velocity produces a Reynold's number in the laminar flow regime (approximately less than about 2200). Thus, bubbles of a selected size, such as greater than about 10 microns in mean size, may be generated without the coating 70 by flowing the saturated liquid through a crimped tubing.

Further, as discussed above, the bubbles generated with the container system 10 including the tube 50 having the coating 70 can allow for the generation of bubbles substantially on demand. That is, the bubbles are not maintained or contained within the container 10 during a period of time. Rather the bubbles 90 are formed as the liquid within the container 10 passes through the tube 50 and encounters the coating 70. The liquid has the gas that forms the bubbles dissolved therein at a selected saturation amount. Thus, no bubbles need be formed and maintained within the container 14. Accordingly, stabilization of bubbles within the container 14 is not required. Thus, the material within the container 14 can be substantially limited to the liquid carrier and the dissolved or saturated gas. For example, the liquid can be substantially sterile saline and the gas can include substantially pure oxygen (e.g., $O_2$) with no other stabilizers, surfactants, or coatings. It is further understood that other liquid carriers can include 5 wt % dextrose or other appropriate liquids, including any biocompatible liquid. Accordingly, the inclusion of stabilizing materials can be substantially eliminated from the delivery of the bubbles. Further, the solution generally including saline or the dextrose water can have a substantially indefinite shelf life when the system 10 is sealed. Thus, the container 14 can be filled with the saturated liquid and maintained in storage for use for a substantially extended period of time.

It is understood, however, that additives can be included. The additives may include surfactants that may allow for the formation of a smaller bubble size than without the surfactant and/or may allow for a longer lived bubble. Addition of one or more surfactants in an aqueous physiologic liquid (e.g., normal saline) within the pressurized container can be used to reduce the size of bubbles 90 generated in an effluent from the distal tip of the tube. Examples of surfactants include nonionic agents, biocompatible, FDA-approved excipients such as polyethylene glycol 40 stearate, poloxamer 188, polysorbitol 80; anionic surfactants such as sodium laurel sulfate; and cationic surfactants such as benzylkonium chloride. According to various embodiments, one or more of the noted additives at a concentration of 0.1 g % in water, saturated with oxygen at 300 psi allowed for a creation of a mean bubble size approximately 5 microns to approximately 10 microns (standard deviation of approximately 2 microns) in an effluent when delivered through a 100 micron internal diameter fused silica tubing, 4 inches long, into host water flowing at 400 mL/min. The size of the bubbles is measured by video-microscopy at approximately 600 times magnification, with a 40 nanosecond strobe light source (Sugawara Labs, Japan) in an effluent flowing at about 5 meters/second to approximately 20 meters/s. The effluent (6 mL/min) was noted to produce dense ultrasound contrast when infused for a few seconds into a 500 mL beaker of water, as noted with a Hewlett-Packard Sonos 1000™ ultrasound system with a 3.5 Mhz probe. Addition of the surfactant in the host water could be used to prolong the echo contrast formed by the bubbles to have a half-life of about 20 to about 30 seconds.

Further, due to the long storage time and the minimal preparation needed to form the bubbles, the system 10 can be used to deliver bubbles in a substantially quick manner. As discussed above, once the liquid is passed through the tube 50, the bubbles 90 are generated. Accordingly, an efficient connection of the tube 50 with a selected delivery port, such as an intravenous connection, may be the only action required to introduce bubbles into a subject, including a human subject. Thus, minimal preparation, minimal training, and rapid delivery of the bubbles can be achieved. Thus, providing the bubbles 90a as an echogenic contrast agent can be substantially quick and not require extensive training to be achieved.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system to generate a plurality of bubbles, comprising:
   a container having a container wall formed around an internal volume configured to hold a liquid saturated with a gas;
   a tube extending from a first end to a second end having a tube wall surrounding a throughbore, wherein an inner surface of the tube wall is substantially smooth; and
   a hydrophobic domain formed at the second end of the tube, wherein the first end of the tube is interconnected with the container;
   wherein the hydrophobic domain is formed by a coating of a gallium alloy.

2. A system to generate a plurality of bubbles, comprising:
   a container having a container wall formed around an internal volume configured to hold a liquid saturated with a gas;
   a tube extending from a first end to a second end having a tube wall surrounding a throughbore, wherein an inner surface of the tube wall is substantially smooth; and
   a hydrophobic domain formed at the second end of the tube, wherein the first end of the tube is interconnected with the container;
   wherein the hydrophobic domain is formed by a coating of gallium.

3. A system to generate a plurality of bubbles, comprising:
   a container having a container wall formed around an internal volume configured to hold a liquid saturated with a gas;
   a tube extending from a first end to a second end having a tube wall surrounding a throughbore, wherein an inner surface of the tube wall is substantially smooth; and
   a hydrophobic domain formed at the second end of the tube, wherein the first end of the tube is interconnected with the container and the second end is free;
   wherein the hydrophobic domain includes an area of a plurality of hydrophobic domains that extend at most 2 mm into the throughbore of the tube along the inner surface of the tube wall.

4. The system of claim 3, wherein the hydrophobic domain includes an area of a plurality of hydrophobic domains that extend about 1 mm into the throughbore of the tube along the inner surface of the tube wall.

5. The system of claim 3, wherein the container is sized to hold 50 ml of the liquid.

6. The system of claim 3, further comprising:
   a nozzle having a valve to selectively release the liquid from the container through the tube.

7. A system to generate a plurality of bubbles, comprising:
   a container having a container wall formed around an internal volume configured to hold a liquid saturated with a gas;
   a tube extending from a first end to a second end having a tube wall surrounding a throughbore, wherein an inner surface of the tube wall is substantially smooth; and
   a hydrophobic domain formed at the second end of the tube, wherein the first end of the tube is interconnected with the container and the second end is free;
   wherein the tube has an internal diameter of at most about 100 micrometers.

8. The system of claim 7, wherein the tube is dimensioned to allow laminar flow therethrough at a selected initial pressure of the liquid within the container when released through the tube.

9. A system to generate a plurality of bubbles, comprising:
   a container having a container wall formed around an internal volume configured to hold a liquid saturated with a gas;
   a tube extending from a first end to a second end having a tube wall surrounding a throughbore, wherein an inner surface of the tube wall is substantially smooth; and
   a hydrophobic domain formed by a coating at the second end of the tube;
   wherein the first end of the tube is interconnected with the container and the second end is free;
   wherein the coating is a gallium alloy.

10. A system to generate a plurality of bubbles, comprising:
    a container having a container wall formed around an internal volume configured to hold a liquid saturated with a gas;
    a tube extending from a first end to a second end having a tube wall surrounding a throughbore, wherein an inner surface of the tube wall is substantially smooth; and
    a hydrophobic domain formed by a coating at the second end of the tube;
    wherein the first end of the tube is interconnected with the container and the second end is free;
    wherein the coating is gallium.

11. A system to generate a plurality of bubbles, comprising:
    a container having a container wall formed around an internal volume configured to hold a liquid saturated with a gas;
    a tube extending from a first end to a second end having a tube wall surrounding a throughbore, wherein an inner surface of the tube wall is substantially smooth; and
    a hydrophobic domain formed by a coating at the second end of the tube;
    wherein the first end of the tube is interconnected with the container and the second end is free;
    wherein the hydrophobic domain includes an area of a plurality of hydrophobic domains that extend at most 2 mm into the throughbore of the tube along the inner surface of the tube wall.

12. The system of claim 11, wherein the hydrophobic domain includes an area of a plurality of hydrophobic domains that extend about 1 mm into the throughbore of the tube along the inner surface of the tube wall.

13. The system of claim 11, wherein the tube has an internal diameter of at most about 100 micrometers.

14. The system of claim 13, wherein the tube is dimensioned to allow laminar flow therethrough at a selected initial pressure of the liquid within the container when released through the tube.

* * * * *